United States Patent [19]

Dahms

[11] 4,207,166

[45] Jun. 10, 1980

[54] METHOD AND APPARATUS FOR ELECTROPHORESIS

[76] Inventor: Harald Dahms, 22 Lakeview Rd., Ossining, N.Y. 10562

[21] Appl. No.: 804,924

[22] Filed: Jun. 9, 1977

Related U.S. Application Data

[63] Continuation of Ser. No. 667,403, Mar. 16, 1976, abandoned, which is a continuation of Ser. No. 392,760, Aug. 29, 1973, abandoned, which is a continuation of Ser. No. 122,310, Mar. 9, 1971, abandoned.

[51] Int. Cl.$^2$ .................... G01N 27/26; G01N 27/28
[52] U.S. Cl. ........................... 204/299 R; 204/180 G
[58] Field of Search ............... 204/180 G, 180 S, 299, 204/300, 301

[56] References Cited

U.S. PATENT DOCUMENTS

| | | | |
|---|---|---|---|
| 3,399,127 | 8/1968 | Rand et al. | 204/180 G |
| 3,523,863 | 8/1970 | Juhos | 204/299 X |
| 3,554,894 | 1/1971 | Zemel | 204/299 |
| 3,844,918 | 10/1974 | Cawley | 204/180 G |

Primary Examiner—Arthur C. Prescott

[57] ABSTRACT

A plate for use in electrophoresis, comprising a membrane coated with a layer of an electrophoretic medium such as agarose gel. The membrane is bonded to a supporting sheet having cutouts in which the electrophoresis is performed. A transport apparatus moves the plates through an electrophoresis bath into an optical scanning densitometer.

20 Claims, 8 Drawing Figures

METHOD AND APPARATUS FOR ELECTROPHORESIS

This is a continuation of application Ser. No. 667,403 filed Mar. 16, 1976, and now abandoned, which is a continuation of application Ser. No. 392,760 filed Aug. 29, 1973, and now abandoned, which is a continuation of application Ser. No. 122,310 filed Mar. 9, 1971, and now abandoned.

This invention relates to electrophoresis and, more particularly, to the use of thin gel films for electrophoresis.

Electrophoresis is a well known method for the separation of electrically charged species, utilizing the differences in rate of migration in an electrical field. Electrophoresis is, for example, widely used in the analysis of sorum proteins. Most analytical electrophoresis methods use the principle of zone electrophoresis. A thin zone of the sample is applied to the electrophoretic medium. The electrophoretic migration splits this starting zone into fractional zones. The quantity of protein in each fraction is then determined either by colorizotric or fluorometric methods or by measuring the absorption of ultraviolet light by proteins. It is desirable to perform the electrophoretic separation in a minimum of tine with a maximum degree of separation. Electrophoretic separations are currently being performed on a wide variety of electrophoretic media. One class of such electrophoretic media utilizes gel films such as agarose gel films. The use of a thin gel film supported on a plastic base is, for example, described in U.S. Pat. No. 3,479,265. The plastic base supports the agarose film and keeps it in rectangular shape so that it can be easily handled.

I have now found that I obtain improved operating characteristics by using a gel film on an extremely thin and flexible membrane. Such membrane is so flexible and thin that it curls up and wrinkles and cannot be kept in a flat stretched shape when handled. I am providing a frame which is permanently bonded to the membrane to keep the membrane, carrying the gel, stretched and wrinkle-free. The frame may also serve to act as boundary for the gel film. I have found it to be important that the electrophoretic separation is performed where the membrane is not supported by or bonded to the frame. After electrophoresis, the separated fractions may be determined by measuring their absorption of ultraviolet light through the membrane. The electrophoresis plate consisting of the membrane bonded to the frame may be adapted for use in a transport system which moves the plate through an electrophoresis bath into an apparatus for measuring the absorption of ultraviolet light.

It is an object of the invention to provide an electrophoresis plate on which electrophoretic separations can be performed with a high degree of separation.

It is another object of the invention to povide an electrophoresis plate on which the separated fractions can be determined by measuring the absorption of ultraviolet light.

It is still another object of the invention to provide a transport apparatus which moves electrophoretic plates through an electrophoretic bath to an optical scanning apparatus.

These and further objects and avantages of the invention will become more apparent upon reference to the following specification and claims and appended drawings wherein:

DETAILED DESCRIPTION OF THE PREFERRED EMBODIMENTS

Figure 1:
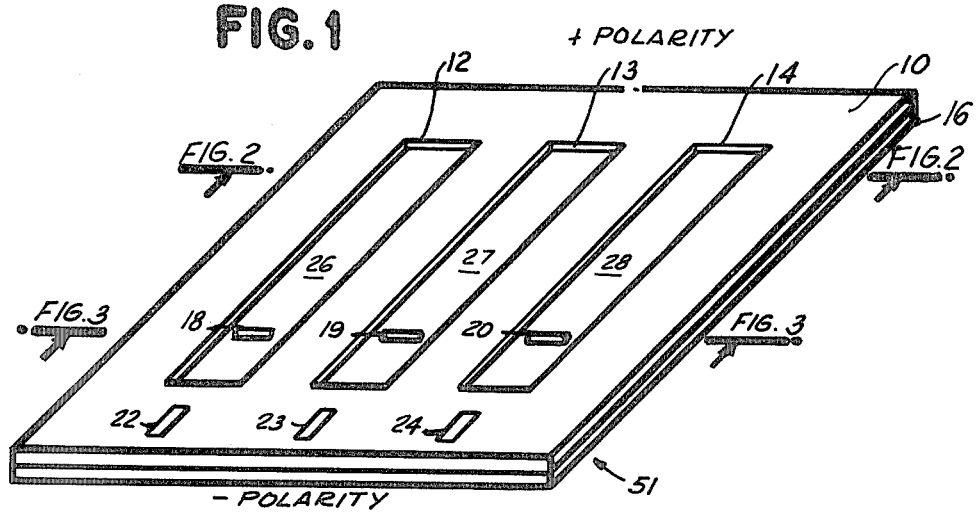
FIG. 1 is a view of a plate for performing electrophoretic separations thereon.

Referring now to FIG. 1, there is shown, generally indicated at 51, a plate for use in electrophoresis. Sheet 10 is bonded to membrane 16. Sheet 10 acts as a frame to stretch membrane 16. Membrane 16 is preferably less than 0.05 mm in thickness and is so thin and flexible that it cannot maintain itself in a flat plane when held on one side. I have used, for example, "Clear Food Wrap 200", sold by Shop-Rite Supermarkets in rolls of 200 feet, 11 ¾ inches wide, having a thickness of 0.008 mm. I have also used "Saran Wrap" made by Dow Chemical Co. in rolls of 100 feet, 11 ¼ inches wide, having a thickness of about 0.015 mm. "Saran" consists mainly of polyvinylidene chloride. It is the generic term for thermoplastic resins obtained by the polymerisation of vinylidene chloride with lesser amounts of other unsaturated compounds. Sheet 10 has rectangular cutouts 12, 13, and 14. Sheet 10 is typically 0.25 mm in thickness. A typical length of each cutout is 75 mm, the width 10 mm. I have used materials such Lucite or Mylar as sheet 10. Membrane 16 is bonded to sheet 10 with a suitable adhesive. I have used, for example, "Epoxy 220", made by Hughes Associates, Excelsior, Minnesota.

Cutouts 12, 13 and 14 are filled with a layer of an electrophoretic medium having a typical thickness of 0.25 mm. I prefer agarose gel as electrophoretic medium. The thickness of the layer of the electrophoretic medium and the thickness of sheet 10 may be identical so that the upper edges of the layer and of sheet 10 are at the same level. The layer of the electrophoretic medium may contain sample wells 18–20 which are formed by commonly known methods. Sheet 10 may also carry markers 22–24 which are used to actuate a densitometer to scan the completed electrophorograms. Markers 22–24 may be either opaque to trigger an optical signal or they may be small means to actuate mechanical sensing switches. Each cutout, filled with the electrophoretic medium, may also be used for the electrophoresis of more than one sample, with a sample well being provided for each sample. The number of three cutouts in each plate is just given as example. There may be more or fewer cutouts per plate. When it is desired to measure the absorption of ultraviolet light caused by the presence of protein fractions by measuring the transmittance of light through the membrane and the electrophorotic medium, I prefer to use agarose gel made up with buffer solutions of low ultraviolet light absorption. Such buffers are commonly known.

It should be noted that the electrophoretic migration on the plates proceeds in the electrophoretic medium supported only by the thin membrane 16, but not by sheet 10. I have found that this feature provides for the excellent sharpness of the separations. It also provides for a method of directly measuring the absorption of ultraviolet light through the electrophoretic medium when membrane 16 is chosen to have a minimum absorption of ultraviolet light. The "Saran" membranes mentioned above are especially suited for this purpose.

Figure 2:
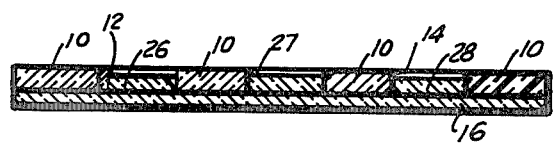
FIG. 2 is a view in cross section of the plate shown in FIG. 1.

FIG. 2 which is a cross sectional view of FIG. 1 shows the layers of the electrophoretic medium, 26, 27, and 28. They are confined by plastic sheet 10 and membrane 16.

Figure 3:
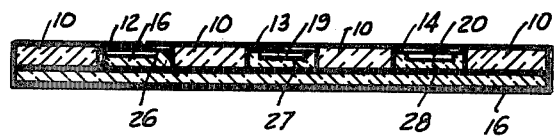
FIG. 3 is a cross sectional view of the plate shown in FIG. 1.

FIG. 3 is a cross sectional view of FIG. 1, showing sample wells 18, 19, and 20 in the layers of the electrophoretic medium 26, 27, and 28.

Figure 4:
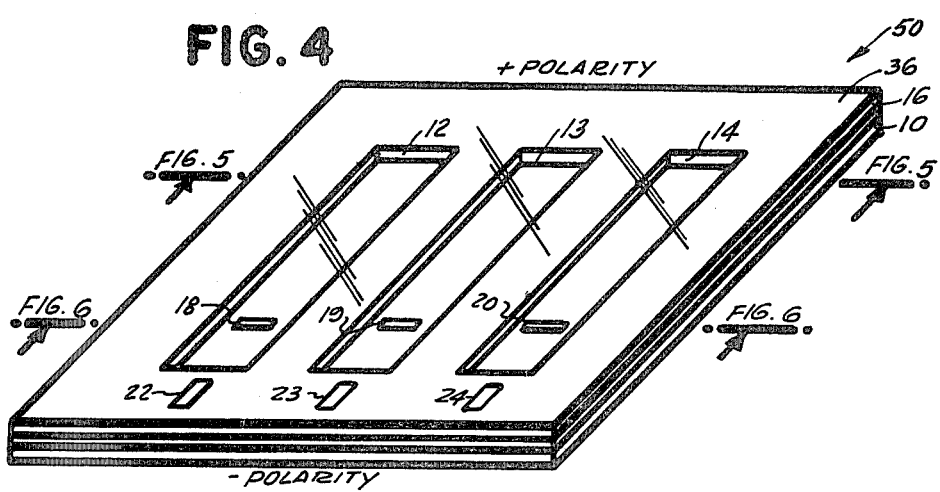
FIG. 4 is a view of another embodiment of the plate for performing electrophoretic separations thereon.

FIG. 4 shows another embodiment of an electrophoresis plate, generally indicated at 50. Membrane 16 is bonded to sheet 10. A continuous layer of the electrophoretic medium, 36, covers the membrane. Sample wells 18, 19, and 20 are provided in the layer of the electrophoretic medium.

Figure 5:
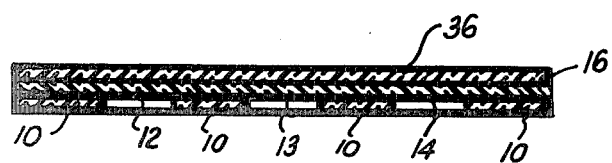
FIG. 5 is a cross sectional view of the plate shown in FIG. 4.

FIG. 5 shows a cross sectional view of FIG. 4. Layer 36 is on top of membrane 10 having cutouts 12, 13, and 14.

Figure 6:
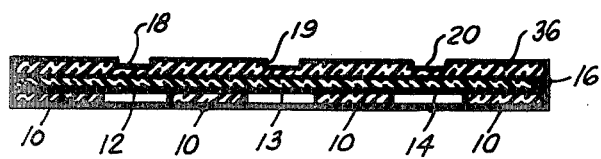
FIG. 6 is a view in cross section of the plate shown in FIG. 4.

FIG. 6 shows a cross section of FIG. 4. Sample wells 18, 19 and 20 are shown in layer 36.

It should be noted that in the embodiment shown in FIG. 4, as well as in that shown in FIG. 1, the electrophoresis proceeds in the layer of electrophoretic medium supported only by membrane 16 and not by sheet 10.

It is understood that membrane 16 may be bonded to sheet 10 by suitable adhesives by heat sealing, by mechanical means such as clamping or by other means.

The preferred electrophoretic medium is agarose since it provides for excellent separation and for high optical transmittance of ultraviolet light. However, other electrophoretic media such as agar gel or acrylamide gel may be used in the present structure. It is preferred to use gels which have no fluid characteristics. Such fluid characteristics appear when gels are used with low concentrations of the gelling agent. Agarose, for example, has fluid characteristics when below ~0.1% concentration. I prefer to use agarose in concentrations higher than 0.2%, most preferably about 1% concentration by weight.

Figure 8:
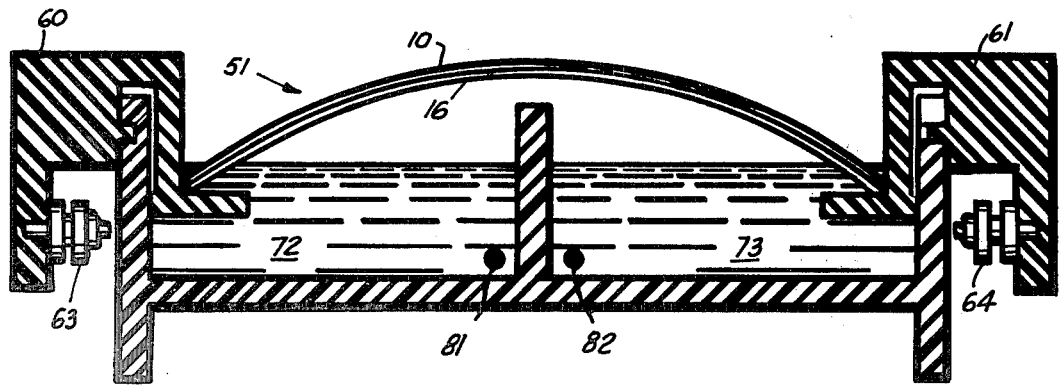
FIG. 8 is a cross sectional view of the apparatus shown in FIG. 7.

In operation, the samples to be analyzed, typically 1-2 microliters, are introduced into sample wells 18-20 of plate 51. Electrolytic contact is established between plate and electrophoresis bath, with the polarity of the electric field in the direction as shown in FIG. 1. The electrophoresis plate may be bent as shown in FIG. 8 to establish contact. Other means of establishing contact by wicks etc. are known. The electric field is now applied until the fractions are separated. For the quantitative determination of the fractions I prefer optical measurements with ultraviolet light. However, other known means such as fluorometry or colorimetry may be used. It is common knowledge that proteins absorb ultraviolet light in several wavelength ranges, the strongest absorption being at about 205 nanometers. I prefer to use this wavelength range. Densitometers for scanning electrophoresis strips are known. The scanning is performed in the direction of the long axis of cutouts 12-14 which is also the direction of electrophoresis. The light beam is transmitted through membrane 16 and through layer 26 of the electrophoretic medium which is preferably agarose. The direct scanning of the layer 26 by measuring the light transmittance is an important aspect of the invention which is possible through the use of thin membrane 16 which is sufficiently transparent for ultraviolet light.

Figure 7:
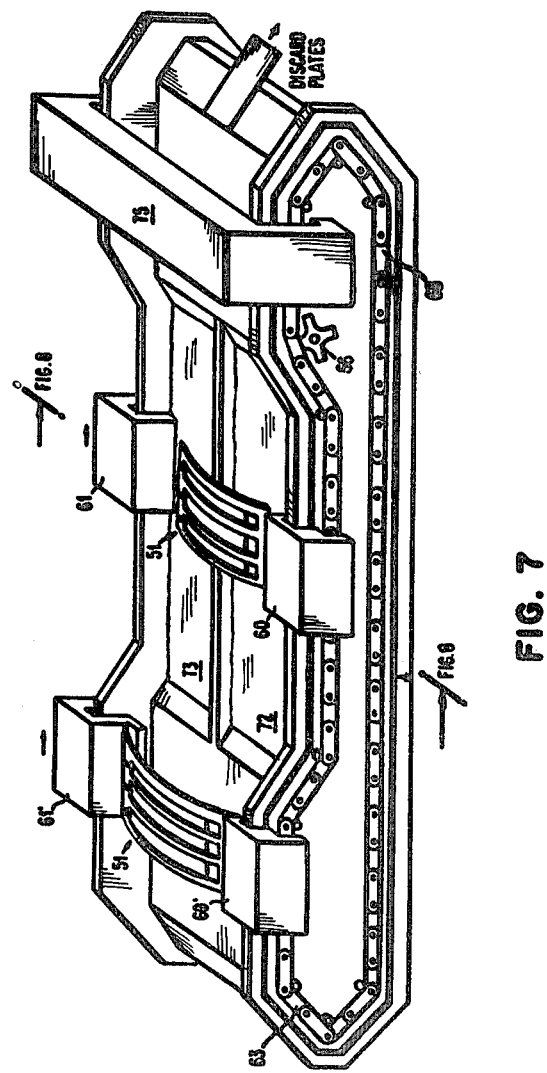
FIG. 7 is a view of a transport apparatus to move electrophoresis plates through an electrophoresis bath into an optical densitometer.

The electrophoresis plates may be used in the apparatus shown in FIG. 7. Plate 51 is held in a bent position by holders 61' and 60'. Holders 61' and 60' are connected to circular chains 63 and 64, respectively. Chain 64, being in the rear of the apparatus, cannot be seen in FIG. 7. Chain 63 is driven by sprocket 66 with a motor (not shown) which also drives chain 64 with a similar sprocket at the same speed. There is also shown another pair of holders, 60 and 61. In actual operation there will be a multitude of holder pairs all along chain 63. After application of samples on to plate 51 it is transported downwards into electrophoresis baths 72 and 73 so that the two opposite edges of plate 51 establish electrolytic contact. Bath 72 is connected to the negative outlet of a common electrophoresis power supply while bath 73 is connected to the positive outlet. The duration of the electrophoresis is determined by the speed of chain 63 and by the length of electrophoresis bath 72. After the appropriate time the plate is moved upward and out of the electrophoresis bath into densitometer 75. Densitometer 75 may be actuated by markers 24, 23, and 22 as they enter the densitometer. After scanning of the electropherograms plate 51 is discarded by automatically removing it from holders 61 and 60.

FIG. 8 shows a cross sectional view of FIG. 7. Plate 51 is resting in a bent position on holders 60 and 61 which are connected to chains 63 and 64, respectively. Plate 51 is contacting electrophoretic baths 72 and 73. Wire 81 is located in bath 72 to apply a negative voltage and wire 82 is located in bath 73 to apply a positive voltage from a power supply (not shown).

When agarose gel or another gel is used as the electrophoretic medium care must be taken to preserve the water content of the gel layer. The plate may be stored in an appropriate sealed container until use. Alternatively, the gel film may be dried after manufacture of the plate. The gel film is then restored by soaking it in a buffer solution before use.

It is understood that the foregoing detailed description is merely given by way of illustration and that many variations may be made therein without departing from the spirit of the invention. The "Abstract" given above is merely for the convenience of searchers and is not to be given any weight in defining the scope of the invention.

I claim:

1. An apparatus for electrophoretic analysis of biological samples comprising:
   input means for receiving and holding a plate to be used in said analysis, said plate having an electrophoretic medium and said biological sample thereon,
   support means for supporting an electrophoretic bath which said plate contacts during said analysis,
   electric means for applying an electric field across said plate while said plate is in contact with said bath, said electric means including means for electrically contacting said bath, and
   mechanical means connected to said input means for bringing said plate and said bath into electrolytic contact with one another for a time sufficient to allow electrophoresis to occur and for providing relative motion between said plate and said bath, said electric field being applied in a direction which is transverse to said relative motion to produce electrophoretic separations which extend in a direction transverse to said relative motion.

2. The apparatus of claim 1, where said mechanical means for providing relative motion transports said plate into electrolytic contact with said bath.

3. The apparatus of claim 2, where said direction of transport of said plate is substantially perpendicular to the direction of said applied electric field.

4. The apparatus of claim 1, further including optical scanning means to which said plate is brought by said mechanical means after said electric field is applied thereacross, and for scanning said separations along the direction in which they extend.

5. The apparatus of claim 4, wherein said scanning means includes a source of ultraviolet light.

6. The apparatus of claim 4, where said plate has at least one sample well therein for containing said biological sample.

7. The apparatus of claim 1, including additional input means connected to said mechanical means for receiving additional plates to be used in said electrophoretic analysis.

8. The apparatus of claim 1, further including means for controlling the amount of time during which said plate and said bath are in electrolytic contact with one another.

9. An apparatus for performing electrophoretic analysis of biological samples, comprising:
input means for receiving and holding a plate having an electrophoretic medium and said biological sample thereon,
transport means connected to said input means for moving said plate in a first direction,
electric means for applying an electric field across said plate to produce electrophoretic separations of the components of said sample, said electric means being comprised of electrophoretic baths for applying said electric field across said plate in a direction transverse to the direction of movement of said plate when said plate is brought into electrolytic contact with said baths by said transport means,
optical scanning means for scanning said separations for analysis of said components electrophoretically separated by said electric field when said plate is transported to said scanning means by said transport means.

10. The apparatus of claim 9, where said electric field is applied in a direction substantially perpendicular to the direction of movement of said plate.

11. The apparatus of claim 9, where said means for holding includes means for holding said plate in a bent position, opposing edges of said plate contacting separate electrophoretic baths.

12. The apparatus of claim 11, where said plate has at least one sample well therein for said sample, and said optical scanning means includes a source of ultraviolet radiation which scans said separations.

13. An apparatus for performing electrophoretic analysis of biological samples, comprising:
input means for receiving and holding a plate having an electrophoretic medium and said biological sample thereon,
transport means connected to said input means for moving said plate in a first direction to an electric means and then to an optical scanning means,
electric means for applying an electric field across said plate to produce electrophoretic separations of the components of said sample, said electric field being applied across said plate in a direction transverse to the direction of movement of said plate,
optical scanning means for scanning said separations for analysis of said components electrophoretically separated by said electric field.

14. The apparatus of claim 13, where said optical scanning means includes means for providing ultraviolet radiation for scanning said separations.

15. An apparatus for performing electrophoretic analysis of biological samples, comprising:
input means for receiving and holding a support member containing an electrophoretic medium and said biological sample, said support member being substantially transparent to ultraviolet radiation,
transport means connected to said input means for moving said support member in a first direction to an electric means and then to an optical scanning means,
electric means for applying an electric field across said support member to produce electrophoretic separations of the components of said sample, said electric means being comprised of electrophoretic baths for applying said electric field across said support member in a direction transverse to the direction of movement of said support member when said baths are contacted by said support member,
optical scanning means for scanning said separations with ultraviolet radiation for analysis of said components electrophoretically separated by said electric field.

16. An apparatus for electrophoretic analysis of a biological sample located on an electrophoresis cell having an electrophoretic medium thereon, comprising:
transport means for holding said cell and for moving said cell in response to a control signal, said transport means moving said cell into electrolytic contact with electrophoretic baths and then to an optical scanner,
electric means connected to said baths for providing electrolytic contact thereto when said cell is in electrolytic contact with said baths, said electrolytic contact producing an electric field across said cell in a direction transverse to the direction of movement of said cell to produce electrophoretic separations of the constituents in said biological sample, said separations extending in a direction along said electric field and transverse to said direction of motion of said cell, and
optical scanning means for optically scanning said electrophoretic separations in response to a control signal to determine the constituents in said biological sample.

17. An apparatus for electrophoretic analysis of a sample of body fluid, comprising:
an electrophoresis cell having an electrophoretic medium and said body fluid sample thereon,
transport means for holding said cell and for moving said cell into electrophoretic contact with electrophoretic baths for establishing an electric field across said sample and said electrophoretic medium, said cell being comprised of a plate having portions thereof which are transparent to electromagnetic radiation, where said transport means brings the edges of said plate into electrolytic contact with said baths, electric means including said baths for producing an electric field across said electrophoretic medium and said sample in a direction transverse to the direction of movement of said cell to produce electrophoretic separations of the constituents in said sample, optical scanning means for scanning said separations through said transparent portions of said plate to determine the constituents in said sample.

18. The apparatus of claim 17, where said electromagnetic radiation is ultraviolet light.

19. The apparatus of claim 18, where said plate is sufficiently flexible to be bent for electrolytic contact with said baths at opposing edges thereof.

20. An apparatus for performing electrophoretic analysis of biological samples, comprising:

input means for receiving and holding a cell having an electrophoretic medium and said biological sample thereon, transport means connected to said input means for moving said cell in a first direction to an electric means and then to an optical scanning means, electric means for applying an electric field across said cell to produce electrophoretic separations of the components of said sample, said electric field being applied across said cell in a direction transverse to the direction of movement of said cell, optical scanning means for scanning said separations for analysis of said components electrophoretically separated by said electric field.

* * * * *